US012708781B2

(12) United States Patent
Kiele et al.

(10) Patent No.: US 12,708,781 B2
(45) Date of Patent: Aug. 18, 2026

(54) ADJUSTMENT AID, WIRELESS CONNECTOR ASSEMBLY, AND METHOD FOR MONITORING A POSITION

(71) Applicant: Albert-Ludwigs-Universitat Freiburg, Freiburg (DE)

(72) Inventors: Patrick Kiele, Freiburg (DE); Alina Kohler, Herbertingen (DE); Cristian Pasluosta, Vorstetten (DE); Thomas Stieglitz, Freiburg (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 958 days.

(21) Appl. No.: 17/383,048

(22) Filed: Jul. 22, 2021

(65) Prior Publication Data

US 2021/0346703 A1 Nov. 11, 2021

Related U.S. Application Data

(63) Continuation of application No. PCT/EP2019/083300, filed on Dec. 2, 2019.

(30) Foreign Application Priority Data

Jan. 22, 2019 (DE) ..................... 10 2019 200 740.6

(51) Int. Cl.
*A61N 1/00* (2006.01)
*A61B 5/06* (2006.01)
(Continued)

(52) U.S. Cl.
CPC ................ *A61N 1/37* (2013.01); *A61B 5/068* (2013.01); *A61N 1/37241* (2013.01)

(58) Field of Classification Search
CPC .... A61N 1/37; A61N 1/37241; A61N 1/3752; A61B 5/068; A61B 5/24; A61B 5/686
(Continued)

(56) References Cited

U.S. PATENT DOCUMENTS 4,420,754 A 12/1983 Andermo
11,065,439 B1 * 7/2021 Halpern ................ A61B 5/686
(Continued)

FOREIGN PATENT DOCUMENTS

DE 10 2013 108 733 A1 2/2015
DE 10 2018 219 831 A1 5/2020
(Continued)

OTHER PUBLICATIONS

Machine-generated Abstract of DE 10 2013 108 733, dated Feb. 12, 2015, 1 page.

(Continued)

*Primary Examiner* — Sana Sahand
(74) *Attorney, Agent, or Firm* — Barley Snyder

(57) ABSTRACT

An adjustment aid includes a first adjustment electrode assembly having an excitation electrode and an evaluation electrode, a second adjustment electrode assembly having a reception electrode and a transmission electrode, and a control and evaluation circuit connected to the first adjustment electrode assembly. The first adjustment electrode assembly is arranged on the first component. The second adjustment electrode assembly is arranged on the second component. The control and evaluation circuit supplies the excitation electrode with an excitation signal and taps a measurement signal at the evaluation electrode. The measurement signal depends on a degree of overlap between the first adjustment electrode assembly and the second adjustment electrode assembly. A method for monitoring a position of the first component relative to the second component uses the adjustment aid by comparing the measurement signal with a preset threshold value.

23 Claims, 7 Drawing Sheets

(51) Int. Cl.
*A61N 1/37* (2006.01)
*A61N 1/372* (2006.01)

(58) Field of Classification Search
USPC ........................................................... 607/37
See application file for complete search history.

(56) References Cited

U.S. PATENT DOCUMENTS

| | | | | |
|---|---|---|---|---|
| 2007/0067115 | A1* | 3/2007 | Canegallo | G01R 31/2891 257/E25.013 |
| 2013/0079848 | A1 | 3/2013 | Campbell et al. | |
| 2019/0350489 | A1* | 11/2019 | Ludwin | A61B 5/068 |
| 2020/0078596 | A1* | 3/2020 | Holinski | A61N 1/36125 |
| 2020/0215328 | A1* | 7/2020 | Young | A61N 1/0541 |
| 2020/0346013 | A1* | 11/2020 | Page | H04R 25/558 |
| 2021/0268292 | A1 | 9/2021 | Freiburg | |

FOREIGN PATENT DOCUMENTS

| | | | | |
|---|---|---|---|---|
| EP | 0240020 | A2 * | 10/1987 | G01D 5/2415 |
| EP | 1763078 | A1 | 3/2007 | |
| EP | 2661162 | A2 * | 11/2013 | G01R 31/67 |

OTHER PUBLICATIONS

L. S. Gan, et al., "Properties of the Stimulus Router System, a Novel Neural Prosthesis," "IEEE Transactions on Biomedical Engineering", vol. 57, No. 2, pp. 450-459, Feb. 2010.
P. Kiele, et al. "Design Rules for a Transcutaneous Capacitive Array of Electrode Array for Functional Electrical Stimulation of Peripheral Nerves", "IFESS 2018: A0006", 1 page, not dated.
Program Book, 2nd Annual Conference of the International Functional Electrical Stimulation Society, Nottwil, Switzerland, Aug. 28-31, 2018, 4 pages.
C. Pasluosta, et al. "Toward a Multi-Channel Wireless System for Electrical Stimulation of Peripheral Nerves: Modeling and Simulation of Signal Transmission", "IFESS 2018: A0011:", p. 44, Program Book, 2nd Annual Conference of the International Functional Electrical Stimulation Society, Aug. 28-31, 2018.
P. Kiele et al. "Towards a Capacitive Energy and Signal Supply in Neural Implants: In-Vitro Evaluation of Coupling Behavior through Human Skin", 1 page, not dated.
F. Kohler, et al., "Closed-loop interaction with the cerebral cortex: A review of wireless implant technology," "Brain—Computer Interfaces", vol. 4, No. 3, pp. 146-154, dated Jul. 13, 2017.
PCT International Search Report, International App. No. PCT/EP2019/083300, dated Feb. 6, 2020, 10 pages.

* cited by examiner

ADJUSTMENT AID, WIRELESS CONNECTOR ASSEMBLY, AND METHOD FOR MONITORING A POSITION

CROSS-REFERENCE TO RELATED APPLICATIONS

This application is a continuation of PCT International Application No. PCT/EP2019/083300, filed on Dec. 2, 2019, which claims priority under 35 U.S.C. § 119 to German Patent Application No. 102019200740.6, filed on Jan. 22, 2019.

FIELD OF THE INVENTION

The present invention relates to an adjustment aid, a wireless electrical connector assembly, in particular for the use with implantable components, and to an associated method for monitoring the position of a first component and a second component relative to one another.

BACKGROUND

Recent research and development in the field of neural engineering has resulted in a plurality of active implantable medical devices (AIMD) that can be used in a wide range of applications. These typically consist of a housing that contains control electronics and a battery, implantable electrodes (or arrays of electrodes), and cables for establishing electrical contact with the electrodes and the electronics. The electrodes are used for the electrical stimulation of cells or the detection of physiological signals.

Reversibly detachable connectors (hereinafter also referred to as connectors), which are integrated into the cables, make it possible to separate the individual components. This makes implantation easier and also creates the possibility of replacing defective, improved, or worn parts (e.g. the battery in a cardiac pacemaker which only has a lifespan of 3 to 7 years).

Depending on the respective application, the stimulation or the signals recorded are processed in an implanted or in an external unit. Percutaneous cables are often sufficient for power supply and signal transmission during acute interventions. This is avoided in chronic applications as percutaneous cables pose a serious risk of inflammation. For chronic applications, it is preferable to use a wireless transcutaneous transmission system. Examples of such systems are cochlear implants or the so-called Brindley stimulator (bladder pacemaker) which typically use an inductive coupling for both the energy supply as well as the signal transmission on one or more coupling channels.

Resistive or capacitive coupling through the skin is a further alternative. A stimulus router system (SRS) is known, for example, from the article L. S. Gan and A. Prochazka, "Properties of the stimulus router system, a novel neural prosthesis," "IEEE transactions on biomedical engineering", vol. 57, no. 2, pages 450-459, 2010, in which a stimulation current is provided via self-adhesive surface electrodes that are glued to the skin. A subcutaneous reception electrode receives this signal and forwards it to the stimulation site via implanted leads. This concept can be extended to multi-channel applications in which a surface array of electrodes is capacitively coupled with an implanted subcutaneous counterpart in an identical geometric arrangement. Each pair of electrodes then forms a capacitively coupled unit and forms a channel.

Other such concepts are known from P. Kiele et al. "Design Rules for a Transcutaneous Capacitive Array of electrodes for Functional Electrical Stimulation of Peripheral Nerves", "IFESS 2018: A0006", page 35, Program Book, 2nd Annual Conference of the International Functional Electrical Stimulation Society, 28. -31.08.2018, Notwill, C H; C. Pasluosta et al. "Toward a Multi-Channel Wireless System for Electrical Stimulation of Peripheral Nerve: Modeling and Simulation of Signal Transmission", "IFESS 2018: A0011:", page 44, Program Book, 2nd Annual Conference of the International Functional Electrical Stimulation Society, 28.-31.08.2018, Notwill, C H, as well as P. Kiele et al. "Towards a Capacitive Energy and Signal Supply in Neural Implants: In-Vitro Evaluation of Coupling Behavior through Human Skin", conference contribution to the "Engineering in Medicine and Biology Society Conference" in Hawaii, 2018.

In all of these concepts, the alignment of the external component relative to the implanted component is essential in order to ensure sufficient accuracy and efficiency in the energy supply as well as in the energy transmission. For example, in the article F. Köhler et al., "Closed-loop interaction with the cerebral cortex: A review of wireless implant technology," "Brain-Computer Interfaces", vol. 4, no. 3, pages 146-154, 2017, it is suggested to use magnets to align the external component relative to the implanted member.

The disadvantage of the known arrangements, however, is that the stimulation or detecting devices have no possibility of real-time monitoring with which possible misalignments could be corrected. Such monitoring, however, is of crucial importance for multi-channel applications. While misalignments in inductive systems can be compensated for by using larger external coils, this approach is often limited by the miniaturization of the implant and an increasing risk of cross-talk between the channels. There is therefore a need to provide active monitoring of the alignment of an external component relative to an implanted unit to ensure proper operation of the implant, in particular when a distributed multi-channel array is used.

SUMMARY

An adjustment aid includes a first adjustment electrode assembly having an excitation electrode and an evaluation electrode, a second adjustment electrode assembly having a reception electrode and a transmission electrode, and a control and evaluation circuit connected to the first adjustment electrode assembly. The first adjustment electrode assembly is arranged on the first component. The second adjustment electrode assembly is arranged on the second component. The control and evaluation circuit supplies the excitation electrode with an excitation signal and taps a measurement signal at the evaluation electrode. The measurement signal depends on a degree of overlap between the first adjustment electrode assembly and the second adjustment electrode assembly.

BRIEF DESCRIPTION OF THE DRAWINGS

The invention will now be described by way of example with reference to the accompanying Figures, of which.

DETAILED DESCRIPTION OF THE EMBODIMENT(S)

Figure 1:
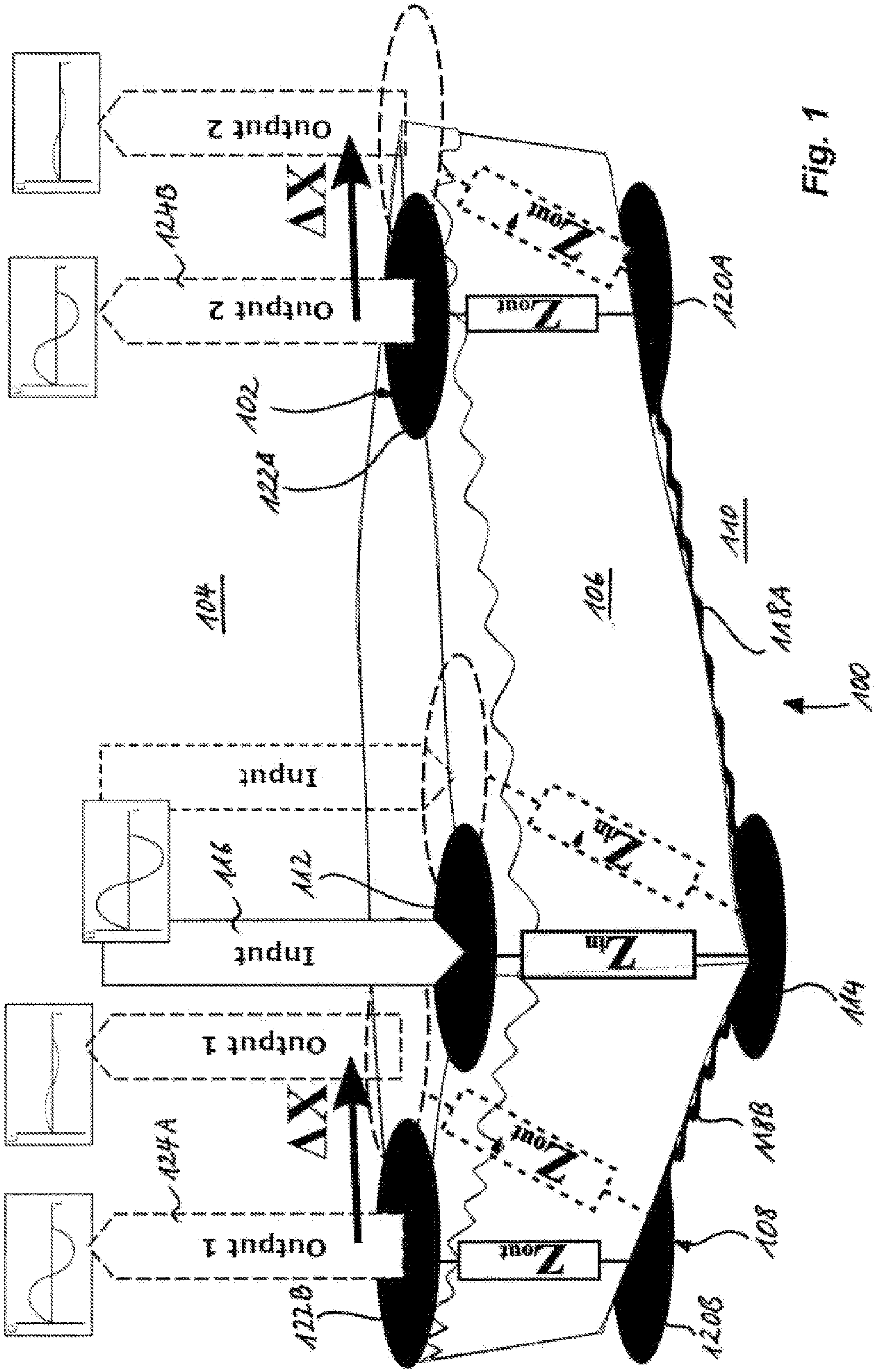
FIG. 1 is a schematic perspective view of an adjustment aid according to an embodiment.

For a better understanding of the present invention, it will be explained in detail with reference to the exemplary embodiments in the figures. Herein, the same parts are provided with the same reference numerals and the same component designations. Furthermore, some features or feature combinations of the shown and described different embodiments can also represent independent inventive solutions or solutions according to the invention.

The principle of adjustment aid 100 according to a first embodiment of the present invention shall first be explained in more detail hereafter with reference to FIG. 1. FIG. 1 shows a perspective view of adjustment aid 100 in the connected state. The adjustment aid 100 aligns a first component and a second component relative to one another.

A first adjustment electrode assembly 102 is located on an outer side 104 of skin 106. A second adjustment electrode assembly 108 is arranged on inner side 110 of skin 106. For example, first adjustment electrode assembly 102 and second adjustment electrode assembly 108 can be parts of a connector which electrically contacts an active implanted medical system (AIMD) through the skin and supplies it with energy; the first adjustment electrode assembly 102 can be arranged on the first component and the second adjustment electrode assembly 108 can be arranged on the second component.

The first adjustment electrode assembly 102 has a first planar array of electrodes and the second adjustment electrode assembly 108 has a second planar array of electrodes which is arranged in a plane parallel to the first planar array of electrodes, when the first and the second component are adjusted relative to one another. With this geometry, the adjustment aid is compatible with planar connectors that are often used for electrically contacting AIMDs. However, it is clear to a person skilled in the art that the principles of the present invention can also be used for other cases of applications in which two parts that are movable relative to one another have to be precisely adjusted relative to one another and one of the two parts that needs to be adjusted is no longer readily accessible after the adjustment electrode assembly has been attached.

In FIG. 1, second adjustment electrode assembly 108 is implanted in a stationary manner in the inner region 110 under skin 106, while first adjustment electrode assembly 102 is displaceable, as symbolized by the dashed elements.

According to the embodiment shown, implanted second adjustment electrode assembly 108 comprises three electrodes that are electrically connected to one another and form a structure similar to that of first adjustment electrode assembly 102. First adjustment electrode assembly 102 comprises three corresponding electrodes not connected to one another on the external unit.

In the embodiment shown in FIG. 1, an excitation electrode 112 of the first adjustment electrode assembly 102 is provided which outputs an excitation signal 116 to corresponding reception electrode 114 of the second adjustment electrode assembly 108. Excitation signal 116 is transmitted capacitively through skin 106 to implanted mating electrode 114. The excitation signal is transmitted to two transmission electrodes 120A, 120B of the second adjustment electrode assembly 108 via electrical connections 118A, 118B. The two transmission electrodes 120A, 120B are arranged such that their connecting lines to the reception electrode 114 intersect at an angle different from 0°. With such an arrangement, both a linear as well as an angular deviation from the ideal position can advantageously be detected. In a particularly advantageous manner, the two imaginary connection axes intersect at 90°, so that an L-shaped electrode geometry is formed. This arrangement has the advantage that the calculation of X and Y components of the position deviations can be calculated particularly easily. With suitable calibration and the use of appropriate evaluation algorithms, other angles are of course also possible if this is necessary, for example, for reasons of space.

From there, a signal is coupled out again capacitively to two corresponding evaluation electrodes 122A, 122B of the first adjustment electrode assembly 102 arranged in outer region 104. The evaluation electrodes 122A, 122B are arranged in such a way that their (imaginary) connecting lines to the excitation electrode 112 intersect at an angle different from 0°. The electrical response, which can be tapped at evaluation electrodes 122 by a control and evaluation unit, forms a measurement signal 124.

The excitation electrode can alternately also function as an evaluation electrode and accordingly the implantable counterpart can function as both a reception as well as a transmission electrode. For example, temporal or spatial inhomogeneities can then be compensated for. For example, electrode 1 excites at time t1, while electrodes 2 and 3 are evaluating. At time t2, electrode 2 excites, while electrodes 1 and 3 are evaluating, etc.

Once misalignment of the component located in outer region 104 relative to the implanted component is given, then coupling impedance Z increases both between the excitation and reception electrodes (Zin) as well as between the transmission and evaluation electrodes (Zout). These increases in impedance lead to a reduction in the electrical response. A conclusion can be drawn about a displacement $\Delta X$ by evaluating measurement signals 124A, 124B. With appropriate calibration, it is also possible to make quantitative statements about the displacement $\Delta X$.

In the optimally adjusted state of the first and the second component relative to one another, the excitation electrode 112 and the reception electrode 114 are aligned to overlap one another to form a feed capacitor, and the transmission electrode 120 and the evaluation electrode 122 are aligned to overlap one another to form a measuring capacitor. Such capacitive coupling has the advantage that no ohmic contact is required. The measurement signal 124 depends on a degree of overlap between the first adjustment electrode assembly 102 and the second adjustment electrode assembly 108.

In this way, it is possible to continuously monitor whether the first and the second component are optimally adjusted relative to one another, even if the second component is no longer readily accessible. In addition, the arrangement can be produced in a simple and inexpensive manner and, in particular, the electrode assemblies can be produced without additional effort together with the electrically conductive structures of the first and the second component that are already present. In addition, the adjustment electrode assemblies take up very little space. This advantage is particularly important for of implanted assemblies.

With the assembly according to the present invention, active monitoring of the alignment of two components relative to one another can be provided that is easy to integrate, wherein one of the two components can be completely electrically passive. Since the input signal and the measured output signal are only applied to or tapped off at one of the two components, the adjustment aid can also be used in places that are difficult to access, or if the layer in between (e.g. the skin) must not be damaged. Finally, the adjustment aid according to the present invention can also be integrated into existing systems.

As will become clear with reference to the following figures, adjustment aid 100 can of course also have other electrode geometries than those shown in FIG. 1. Any arrangement with more than two pairs of electrodes is possible. At least two pairs of electrodes must be provided, but more than two can also be used in order to monitor several degrees of freedom at the same time. The respectively corresponding electrodes are advantageously of the same size and shape. Of course, this is not absolutely necessary, since only the overlap of the oppositely disposed electrodes is included in the measurement signal and the desired measurement signal can be defined by way of appropriate calibration steps in the case of an optimal adjustment.

According to the invention, maintaining the optimal adjustment can be monitored by measuring the electrical response on two transmission channels. The electrical response is proportional to the changes in the coupling impedance. For example, frequencies of more than 1 kHz and low voltages in the range of approximately 1.2 V can be used to prevent nerve pathways or receptors located in skin 106 from being stimulated. Adjustment aid 100 according to the present invention can easily be attached in the vicinity of a stimulation or recording electrode. In addition, the present configuration offers the possibility of simultaneous monitoring of linear displacements within a plane as well as rotatory deviations around any random axis.

Depending on the application, a different physical concept (for example resistive or inductive coupling) can additionally be used instead of a capacitive coupling concept. For example, electrodes that form planar coil arrangements can also be used in addition to or instead of capacitive electrodes.

The coupling electrodes can be formed by alloys such as platinum-iridium or MP35N®. MP35N® is a registered trademark of Standard Pressed Steel Technologies, Inc. The components of MP35N® ensure excellent corrosion resistance of the alloy, as all four alloy components nickel, cobalt, chromium and molybdenum improve the corrosion resistance in almost all stainless steel, nickel and cobalt alloys used in the industry. The proportion of 20% chromium improves the resistance to oxidation, sulphidation, and chemical reactions with salt at elevated temperatures. Any other electrically conductive electrode material can of course also be used. However, only materials that are not ferromagnetic should be used for MRI examinations.

In contrast to ohmic contacts, the electrically conductive coupling electrodes do not have to be opened; i.e. a layer of insulating material can remain thereon. It can be made e.g.

of polymers (Parylene-C, PDMS), oxides (TiOx), or other materials. Parylene-C, for example, is a material approved for human implantation and is electrically tight at a thickness of 10 μm. Various oxides achieve this electrical tightness with significantly less layer thicknesses and have a higher dielectric constant (e.g. εr, $TiO2=63.7$; εr, Paryiene-c=3.1). Both factors promise an increase in the coupling capacity and, accordingly, a better coupling. If no insulation is used, the electrical coupling can take place capacitively and resistively via stored water. In this case, however, adjacent contacts must be insulated from one another. In general, silicone rubber (polydimethylsiloxane, PDMS) is typically selected as the insulator material for use in implantable components. PDMS has the sufficient long-term stability that must be demanded for years of use in an aqueous or moist environment, as it is given for an active implantable assembly. Any other suitable material can of course also be used.

Figure 2:
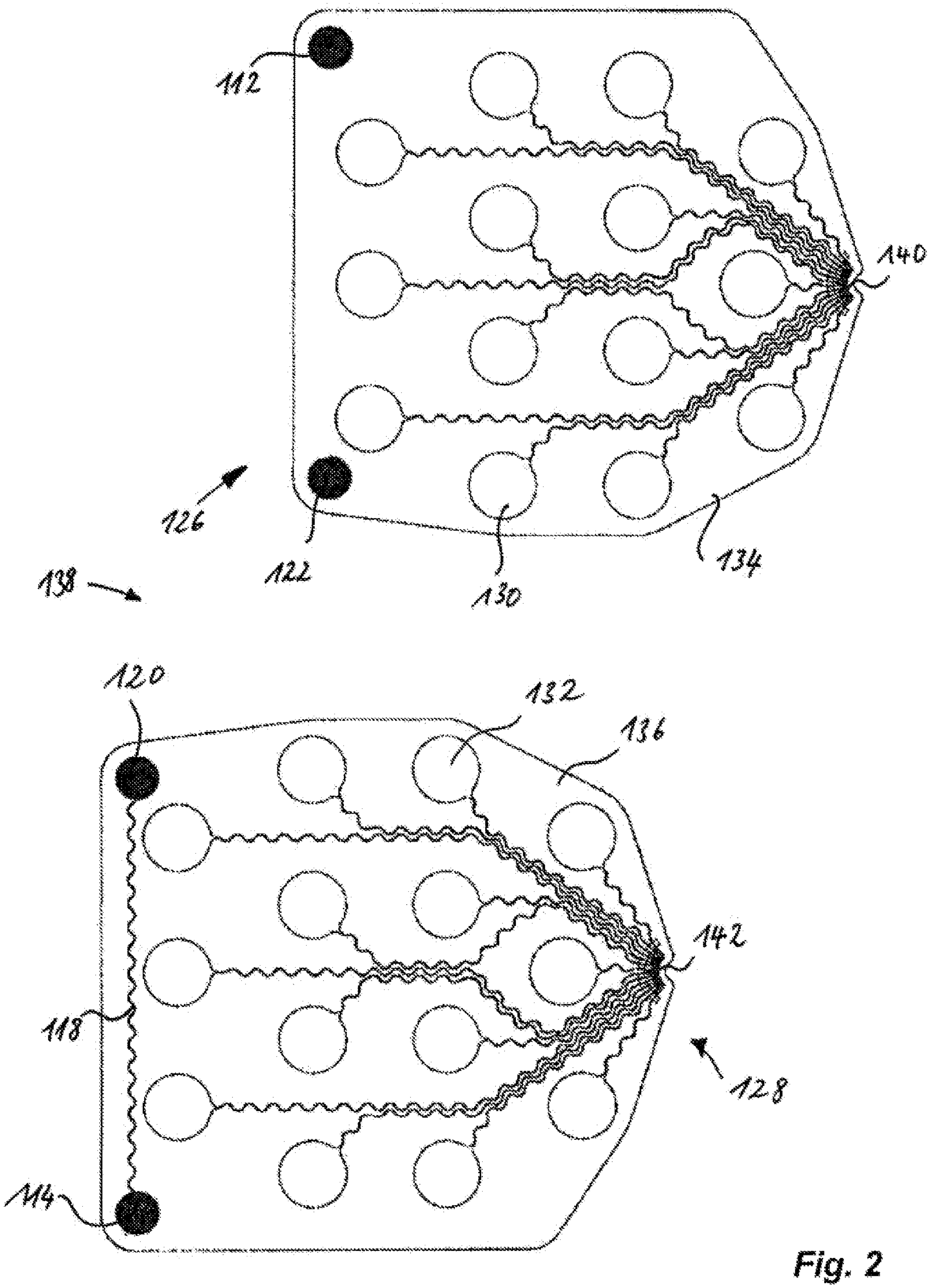
FIG. 2 is a plan view of a capacitive connector assembly with an adjustment electrode assembly according to an embodiment.

FIG. 2 shows an implantable capacitively coupling connector 128 which can be implanted, for example, under the skin and which can establish the connection to a multichannel stimulation electrode assembly or another AIMD. A complementary mating connector 126 is arranged in the immediate vicinity of connector 128 during operation such that the plurality of first coupling electrodes 130 with the corresponding plurality of second coupling electrodes 132 enable capacitively coupled signal transmission. In particular in the case of a large number of connection points to be coupled to one another, it is of essential importance to monitor whether connector 128 is still optimally aligned relative to mating connector 126.

For this purpose, according to the present invention, an adjustment aid is provided which, in the embodiment shown in FIG. 2, is reduced to its simplest components. Implantable connector 128 comprises a reception electrode 114 and a transmission electrode 120. Reception electrode 114 and transmission electrode 120 are connected to one another via an electrically conductive connection 118, for example, a metallized conductor track. In other embodiments, the at least one reception electrode 114 and the at least one transmission electrode 120 can also be coupled in other ways, for example, capacitively by way of comb structures or inductively. The associated first adjustment electrode assembly, which is arranged on connector 126, comprises an excitation electrode 112 and an evaluation electrode 122.

Furthermore, a control and evaluation circuit is provided for monitoring the adjustment of two connectors 126, 128 relative to one another. For this purpose, an excitation signal 116 is applied to excitation electrode 112 by the control and evaluation circuit, as similarly explained above with regard to the first embodiment. It is picked up capacitively through the skin by reception electrode 114 and forwarded to transmission electrode 120 via electrical connection 118. The signal reaches evaluation electrode 122 in a capacitive manner outwardly through the skin. Once first and second connector 126, 128 are no longer sufficiently well aligned, one or both of the capacitive coupling paths lose all or part of the contact and only a weakened measurement signal or no measurement signal at all can be received at evaluation electrode 122.

As already mentioned, the electrodes can be formed by alloys such as platinum-iridium or MP35N®. An electrically insulating passivation layer is provided for the electrical insulation and protection against the external surrounding. First connector 126 and/or second connector 128 in an embodiment have an electrically insulating substrate 134, 136. The substrate material of both connectors 126, 128 can be flexible or rigid depending on the configuration but should not be electrically conductive. Additional insulation layers must be introduced for electrically conductive material. For example, polyimide, PDMS, ceramic and all other materials that are used for electrical circuit carriers are suitable.

Coupling electrodes 130, 132 terminate in connection regions 140, 142 shown in FIG. 2 to which an external circuit or a stimulation electrode can be connected.

Figure 3:
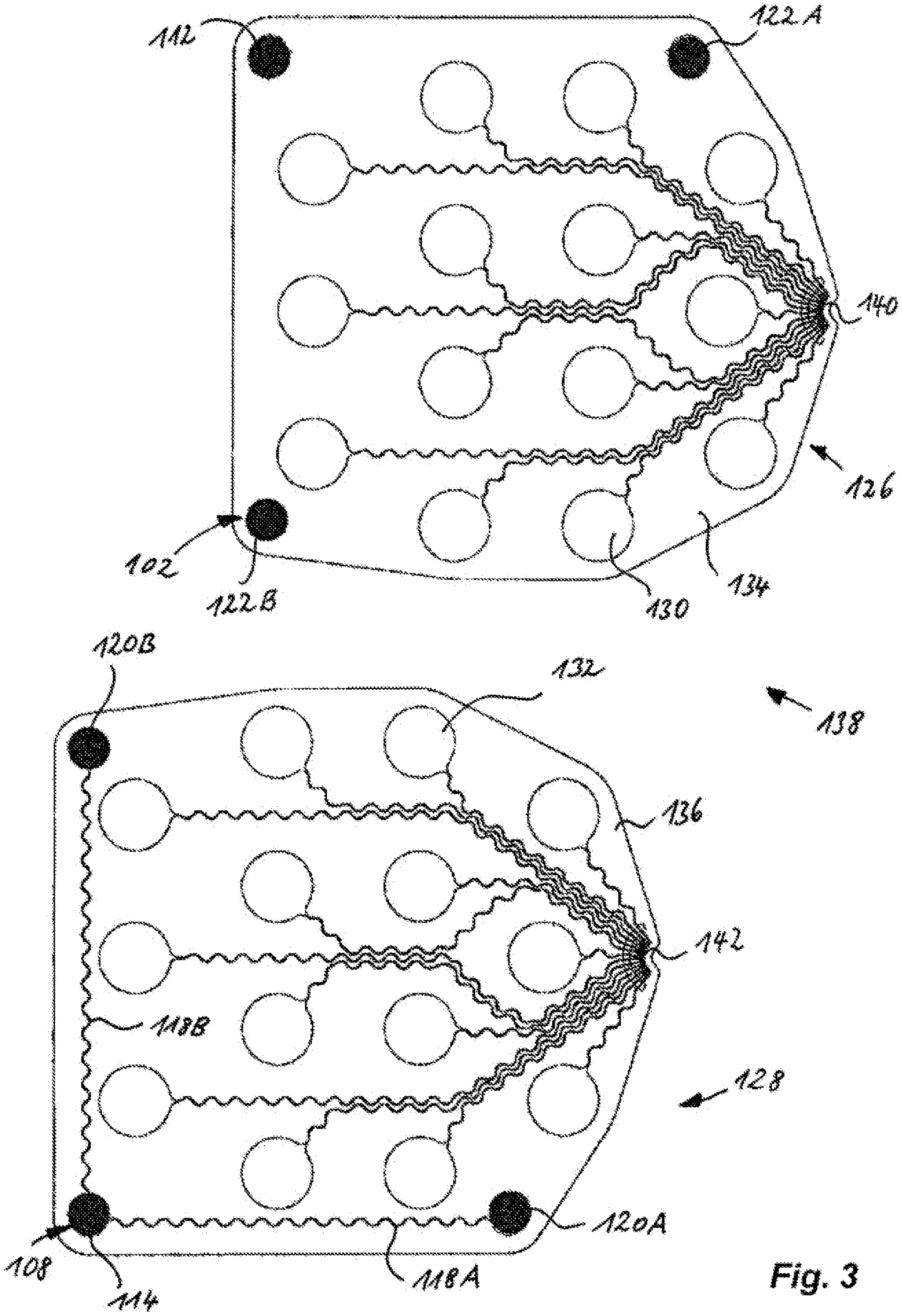
FIG. 3 is a plan view of a capacitive connector assembly with an adjustment electrode assembly according to an embodiment.

Connector assembly 138 in FIG. 3 is shown with a further embodiment of the adjustment aid which corresponds substantially to the L-shaped arrangement from FIG. 1.

According to the embodiment shown in FIG. 3, implanted second adjustment electrode assembly 108 comprises three electrodes that are electrically connected to one another and form an L-shaped structure. First adjustment electrode assembly 102 comprises three corresponding electrodes not connected to one another on external unit 126.

According to the invention, an excitation electrode 112 is provided which outputs an excitation signal 116 to corresponding reception electrode 114. Excitation signal 116 is capacitively transmitted through skin 106 to implanted mating electrode 114. The excitation signal is transmitted to two transmission electrodes 120A, 120B via electrical connections 118A, 118B. From there, a signal is coupled out again capacitively to two corresponding evaluation electrodes 122A, 122B arranged on connector 126. The electrical response, which can be tapped at evaluation electrodes 122 by the control and evaluation unit, forms a measurement signal 124.

If misalignment of connector 126 that is located in outer region 104 relative to implanted component 128 is given, then the coupling impedance increases both between the excitation 112 and reception electrodes 114 as well as between the transmission 120A, 120B and evaluation electrodes 122A, 122B. These increases in impedance lead to a reduction in the electrical response. A conclusion about any displacement or rotation can be drawn by evaluating the measurement signals that can be tapped at evaluation electrodes 122A, 122B. With appropriate calibration, it is also possible to make quantitative statements about the misalignment between two connectors 126, 128.

Figure 4:
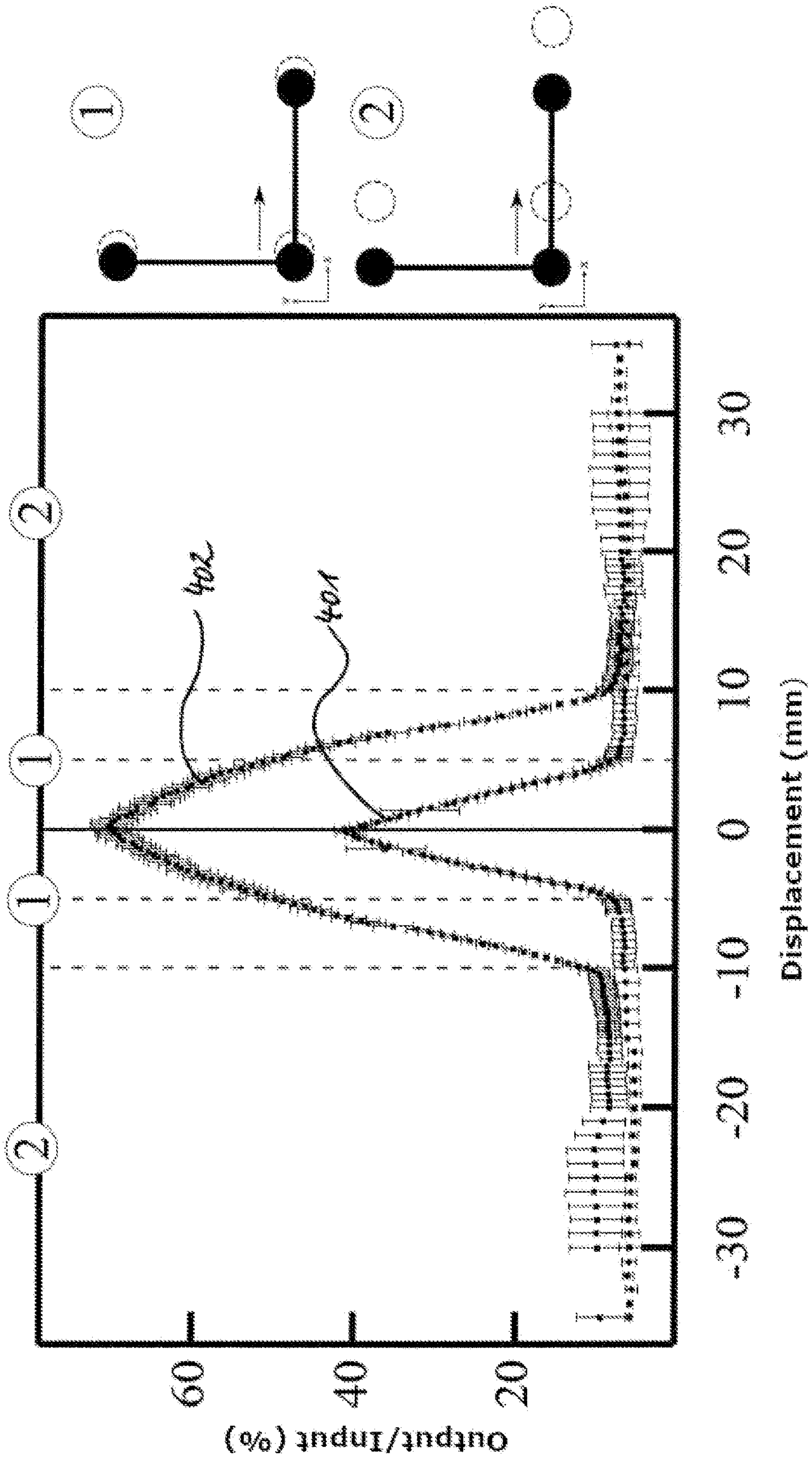
FIG. 4 is a graph of measurement signals in the event of a linear misalignment.
Figure 5:
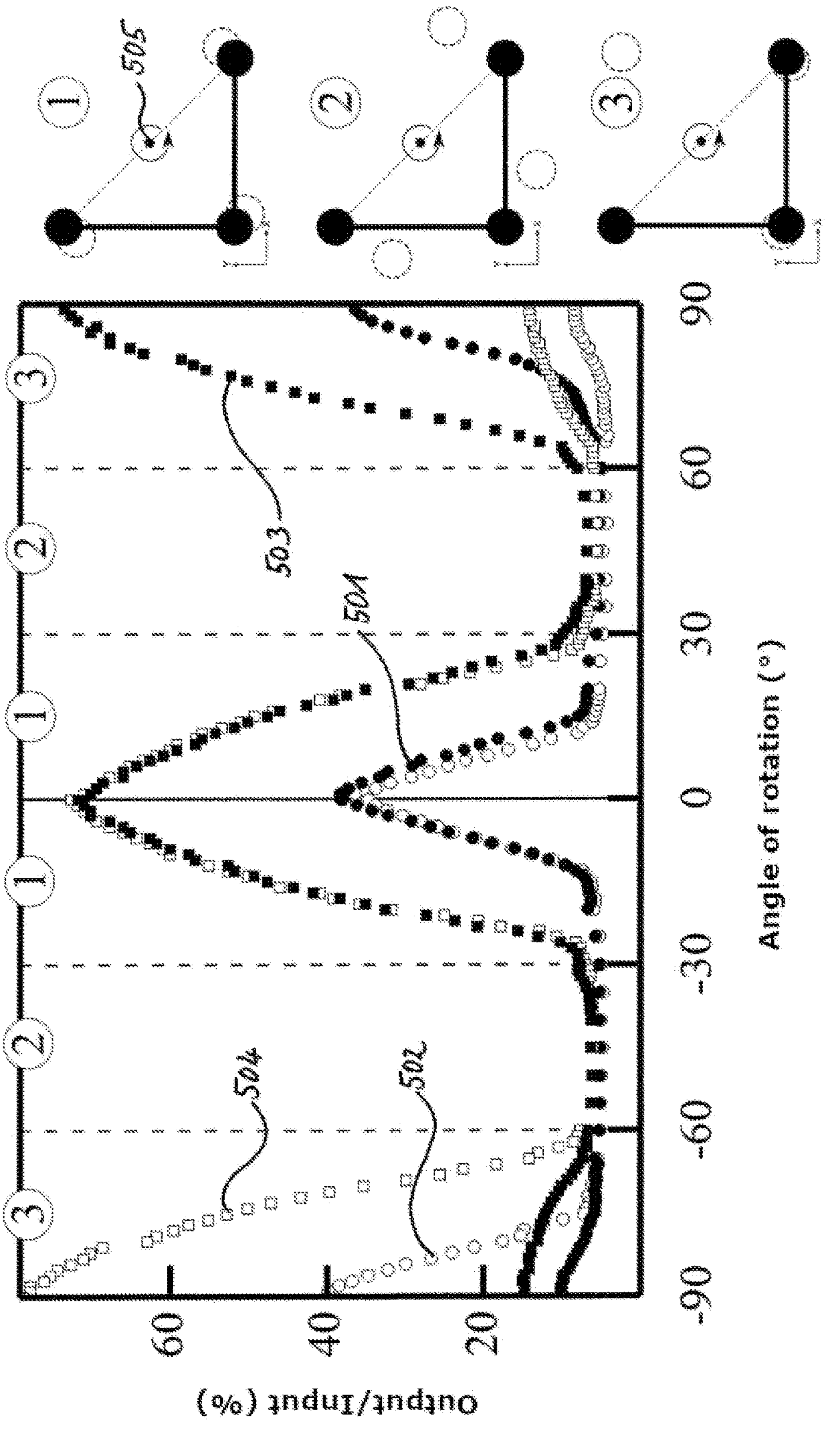
FIG. 5 is a graph of measurement signals in the event of a rotary misalignment.

FIGS. 4 and 5 show measurement results which are obtained with the L-shaped arrangement from FIGS. 1 and 3 using ultrapure water as a model for the skin. When considering FIG. 4, the ratio of the output signal measured to the excitation signal supplied (output/input) is plotted as a function of a linear displacement. Curve 401 shows measurement results for an adjustment aid in which the electrodes have a circular shape with a diameter of 5 mm. Curve 402 shows the corresponding results for circular electrodes with a diameter of 10 mm.

It can be seen that both curves 401, 402 have their maximum at an optimal alignment (i.e. no displacement between the first and the second adjustment electrode assembly and therefore maximum overlap). The losses are less with a larger electrode area, so that a higher output signal can be measured, i.e. the maximum is closer to the ideal value 1. The ratio decreases with increasing displacement between the first and the second adjustment electrode assembly (region 1).

Furthermore, both curves 401, 402 each fall to the minimum base value when the overlap between the first and the second adjustment electrode assembly is no longer present (region 2). The constant base value is due to resistive leakage paths. The behavior shown additionally exhibits rotational symmetry.

FIG. 5 illustrates the results for a pure rotation about a point of rotation 505 which is located at the center of the hypotenuse of the isosceles triangle which is formed by the L-shaped electrodes. Curves 501 and 502 each separately indicate the signals from the evaluation electrodes for an adjustment aid in which the electrodes have a circular shape with a diameter of 5 mm. Curves 503 and 504 show the corresponding results for circular electrodes with a diameter of 10 mm. However, the electrodes can also have a rectangular, oval, triangular, or any other suitable outline shape.

As indicated schematically next to the measurement graph in FIG. 5, three regions can be distinguished. The respective maximum signal is again obtained at an angle of rotation of 0°. All electrodes overlap in region 1. As the angle of rotation increases, this overlap reduces and the signal decreases (region 2). No pairs of electrodes overlap in this region 2, so that the substantially constant base value can be measured there. Finally, in region 3, the excitation electrode overlaps with one of the edge electrodes so that a clear increase in the signal can be recorded. This second peak value is of the same magnitude as a single channel in the case of full alignment. At the same time, the second feedback channel shows a slight increase in the output signal. This behavior was also observed symmetrically for negative angles. The electrodes with the diameter of 5 mm produced a maximum ratio between output and input of about 40%, while the electrodes with the diameter of 10 mm achieved a maximum value of almost 70% percent.

According to the present invention, it can also be provided to predefine a threshold value which the measurement signal (output/input) must exceed for the arrangement to be considered to be sufficiently adjusted. In the event that the value has not been reached, a warning signal can be generated.

The measurement frequency used in these trials was 1 MHz. However, it is not expected that the frequency significantly enters into the measurement results and all suitable frequency ranges can be used for the excitation signals. The best results are expected with frequencies between 1 KHz to 1 MHz.

Figure 6:
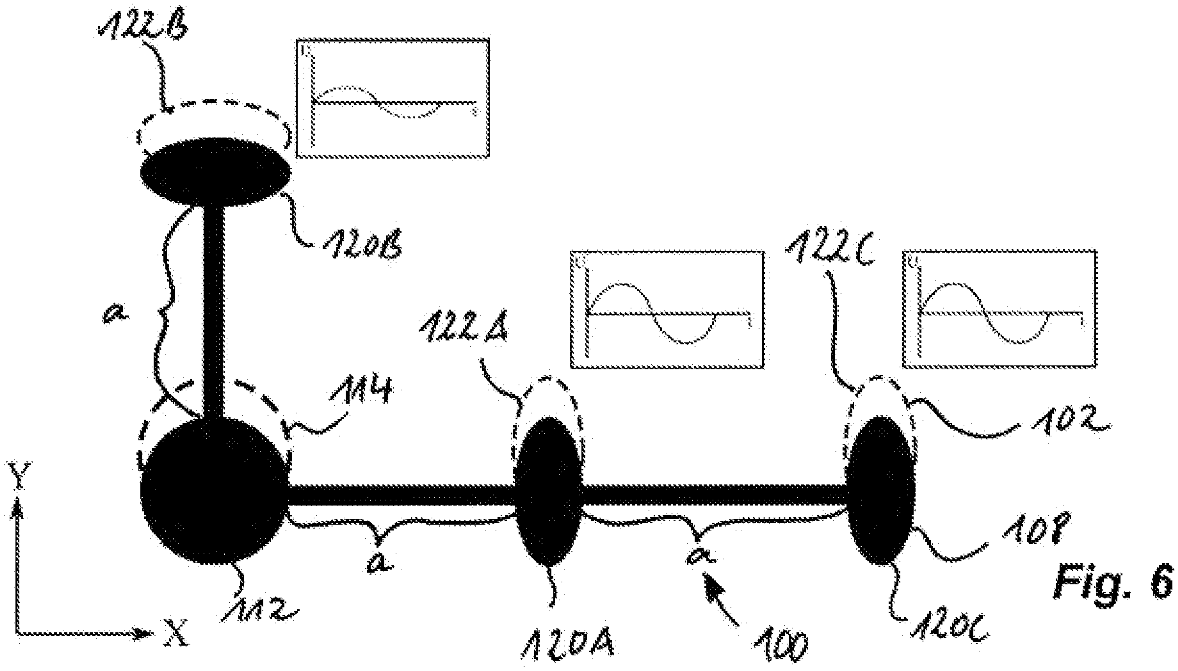
FIG. 6 is a schematic diagram of an adjustment electrode assembly according to an embodiment in the event of linear misalignment.

The measuring principle of an adjustment aid 100 according to a further embodiment shall be explained below with reference to FIGS. 6 and 7. FIG. 6 shows the arrangement for a linear displacement by way of example in the Y direction), whereas FIG. 7 shows a rotation by the angle $\alpha$ about an axis of rotation which coincides with the center of excitation electrode 112.

Figure 7:
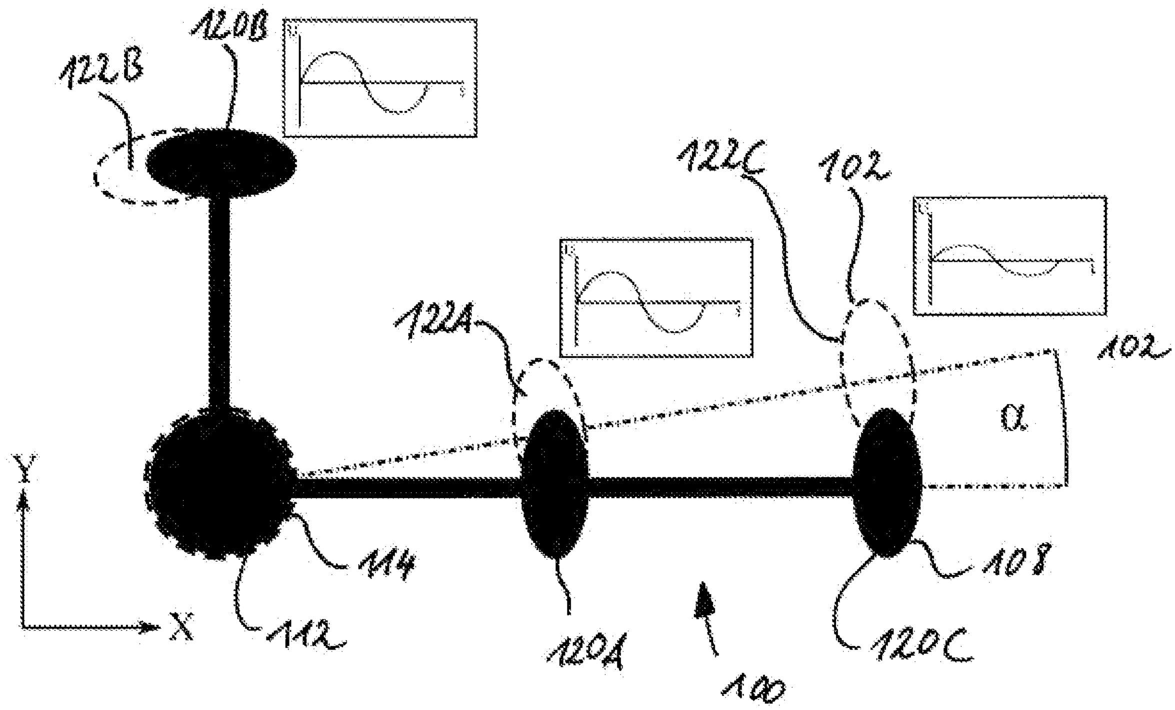
FIG. 7 is a schematic diagram of an adjustment electrode assembly according to an embodiment in the event of rotary misalignment.

Adjustment aid 100 shown in FIGS. 6 and 7 comprises a first adjustment electrode assembly 102 and a second adjustment electrode assembly 108. For example, second adjustment electrode assembly 108 is implanted. According to the embodiment shown, a third evaluation electrode 122C as well as a corresponding third transmission electrode 120C are further provided in addition to excitation electrode 112 and two evaluation electrodes 122A and 122B.

In an embodiment, the third evaluation electrode 122C is not arranged between the second evaluation electrode 122B and the excitation electrode 112, but rather outside. The third evaluation electrode 122C is arranged on the connecting line of one of the pair of evaluation electrodes 122A, 122B and the excitation electrode 112. The evaluation electrodes 122A-C are arranged equidistantly having a spacing on imaginary connecting lines which intersect in excitation electrode 112. In an embodiment, the third transmission electrode 120C is arranged on the connecting line of one of the pair of transmission electrodes 120A, 120B and the reception electrode 114. The transmission electrodes 120A-C are arranged equidistantly from the reception electrode 114.

As shown in FIG. 6, excitation electrode 112 and corresponding reception electrode 114 have a circular shape in an embodiment. Transmission electrodes 120A to 120C and evaluation electrodes 122A to 122C have an elliptical shape in the shown embodiment. For example, the long axis of the ellipse can measure 10 mm while the short axis measures 5 mm. In this way, a distinction can be made between a displacement in the X direction and a displacement in the Y direction. The shape of the electrode according to the present invention can be selected arbitrarily. The excitation electrode 112 and the evaluation electrodes 122 as well as the reception electrode 114 and the transmission electrode 120 can have circular and/or elliptical and/or polygonal metallization structures. They can be produced in a particularly simple manner, e.g. by photo structuring or laser structuring.

With the layout shown in FIGS. 6 and 7, it is also possible to determine the angle of rotation $\alpha$. This is for the reason that the output signal that can be tapped at evaluation electrode 122C drops faster than the output signal that can be detected at evaluation electrodes 122A and 122B.

However, it is of course clear that the dimensions and special values mentioned above are only by way of example and any other suitable geometry and dimensions of the electrodes can also be used, depending on the field of application.

Figure 8:
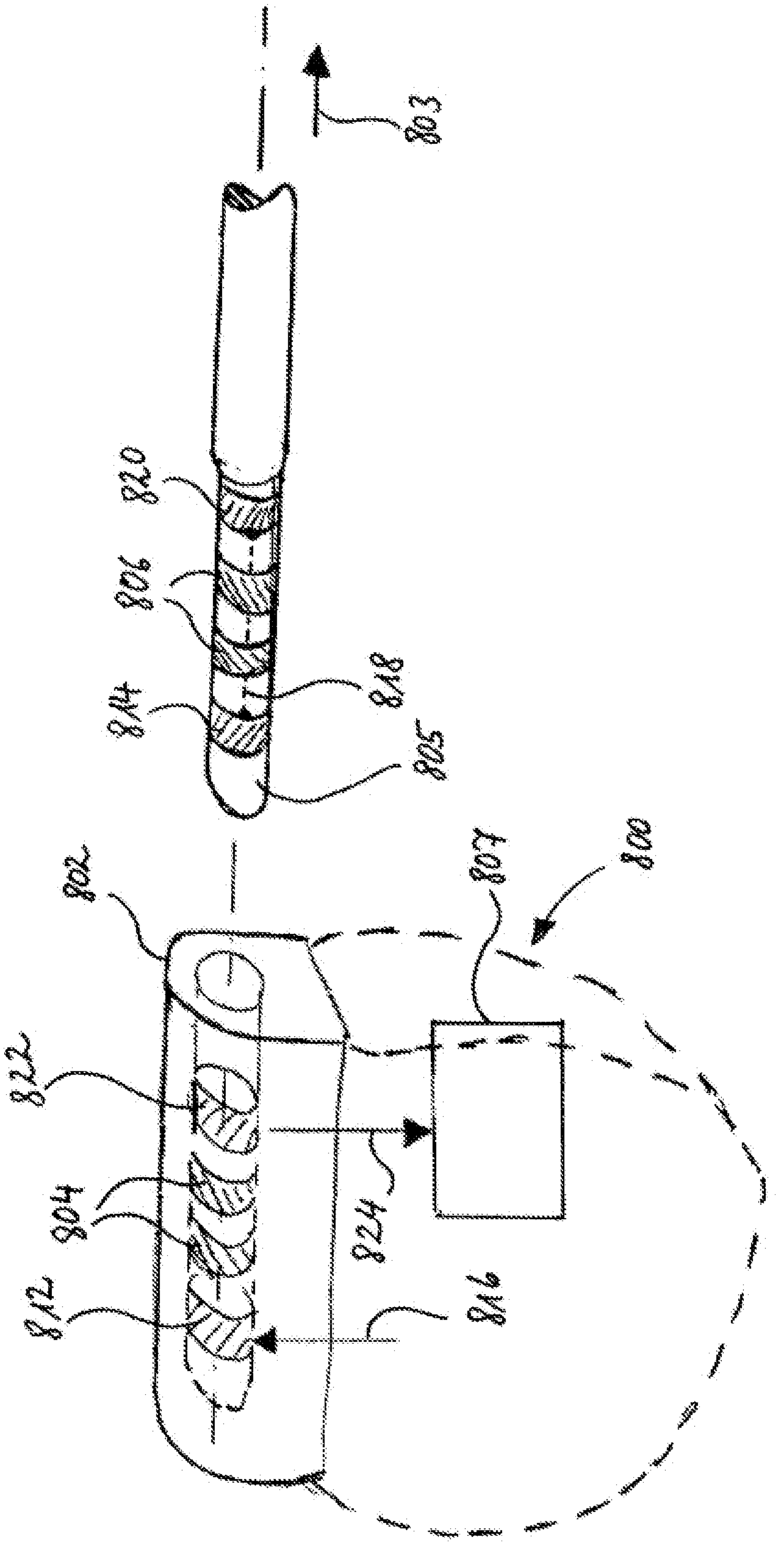
FIG. 8 is a schematic perspective view of a header with an adjustment aid according to an embodiment.

FIG. 8 shows a multi-channel connector for a stimulation implant 800 in which the adjustment aid according to the present invention can be used. For example, the adjustment aid can be used with a cardiac pacemaker, but also with any other implantable systems that comprise and actuate a stimulation electrode (without recording), such as, for example, deep brain stimulators, vagus nerve stimulators, peripheral nerve stimulators, etc. As is generally known, stimulation implant 800 typically has a so-called header or coaxial socket 802 in which electrical connections 804 for the stimulation electrode are arranged. According to the present invention, an excitation electrode 812 and at least one evaluation electrode 822 can be provided in this coaxial connector assembly in addition to connections 804.

According to the principles of the present invention, a reception electrode 814 and a transmission electrode 820 connected thereto are provided in addition to the mating contacts 806 on coaxial plug connector 805, which, as symbolized by the arrow 803, leads to the stimulation electrode. Electrical connection 818 is established in the interior of stimulation electrode connection 804.

As symbolized by arrow 816 in FIG. 8, excitation electrode 812 is acted upon by an excitation signal which in the assembled state is received by reception electrode 814. The signal is transmitted to transmission electrode 820 via electrical connection 818 and coupled to evaluation electrode 822 in a capacitive manner.

Stimulation implant 800 can accordingly read out a measurement signal 824 when plug connector 805 is adjusted to header 802 in a satisfactory manner. In the event that the connection has detached, measurement signal 824 falls below a specified threshold value. Stimulation implant 800 can then, for example, generate and output an alarm signal.

The arrangement shown in FIG. 8 can be used to monitor whether a stimulation electrode is correctly connected to an active implanted stimulation implant. In the event that connector 805 has become detached from header 802, control and evaluation electronics 807 contained in the stimulation implant can generate and output an alarm signal. Potential failure can therefore be recognized in good time.

The present invention is able to provide a robust and precise system for monitoring correct adjustment with which linear and rotatory misalignment of two oppositely arranged electrode assemblies can be detected. Because the implanted structures function as transceivers according to the present invention, the excitation and evaluation can be carried out outside the body so that the system according to the invention can be integrated in any assembly in which direct feedback is not possible. In addition, the present invention is of course not restricted to the adjustment of arrays of electrodes to be implanted externally, but can be used wherever an adjustment has to be monitored and only one of the two partners can directly be electrically contacted.

The adjustment aid allows for aligning at least a first and a second component relative to one another, which allows even densely packed contact arrays to be connected reliably and with an accurate fit. The adjustment aid is inexpensive, is biocompatible, and is certifiable for chronic use. The adjustment aid allows long-term monitoring of the correct alignment.

The advantages of the adjustment aid according to the invention can be used particularly efficiently for a wireless connector unit to an implanted device. The present invention therefore further relates to a wireless connector assembly with a first and a second component and with an adjustment aid according to one of the preceding claims, wherein at least the second component is implantable, and wherein the first component carries a first adjustment electrode assembly and the second component a second adjustment electrode assembly.

In particular, the adjustment aid can advantageously be used when the second component comprises an implantable array of coupling electrodes and the first component comprises an external array of coupling electrodes which establishes electrical contact to the implantable array of coupling electrodes in the implanted state. Such arrays of coupling electrodes can also operate, for example, based on the capacitive principle and are described, e.g. in German patent application DE 10 2018 219 831.4.

According to an advantageous embodiment, the adjustment aid according to the present invention can also be used with coaxial connectors, e.g. with a cardiac pacemaker, but also with any other implantable systems that comprise and actuate a stimulation electrode (without recording), such as deep brain stimulators, vagus nerve stimulators, peripheral nerve stimulators, etc., wherein the first component comprises an implantable coaxial plug connector and the second component comprises an implantable coaxial mating plug connector. For example, the first component is a coaxial socket of a cardiac pacemaker and the second component is the coaxial plug of a stimulation electrode. With cardiac pacemakers there is typically no way of verifying whether the stimulation electrode is actually connected to the header of the actual device. However, the fact that the connector of the stimulation electrode has become detached from the header leads to the failure of the stimulation and thus to the complete (life-threatening) failure of the pacemaker. With the arrangement according to the invention, misalignment between the header and the stimulation electrode connector can already be detected when stimulation signals are still being transmitted to the stimulation electrode, and appropriate countermeasures can be initiated in good time.

The present invention further relates to a method for monitoring the position of a first component and a second component relative to one another, wherein the method uses an adjustment aid according to the present invention and comprises the following steps:

applying an excitation voltage to the at least one excitation electrode, tapping a measurement voltage at the at least one evaluation electrode, comparing the measurement voltage with a preset threshold value.

When misalignment is detected, the method can also provide that the position of the first component and the second component is changed relative to one another until the measurement voltage exceeds the preset threshold value.

Alternatively or additionally, it can also be provided that the control and evaluation circuit generates a warning signal when the measurement voltage is below the preset threshold value. Such warning message is particularly advantageous when used with a chronically implanted device such as a cardiac pacemaker.

What is claimed is:

1. An adjustment aid for aligning a first component and a second component relative to one another, comprising:

a first adjustment electrode assembly having an excitation electrode and an evaluation electrode, the first adjustment electrode assembly arranged on the first component and positioned outside of a human body;

a second adjustment electrode assembly having a reception electrode and a transmission electrode, the second adjustment electrode assembly arranged on the second component and implantable within the human body; and a control and evaluation circuit connected to the first adjustment electrode assembly, the control and evaluation circuit supplies the excitation electrode with an excitation signal and measures a measurement signal at the evaluation electrode, the measurement signal depends on a degree of overlap between the first adjustment electrode assembly and the second adjustment electrode assembly, the degree of overlap is measured perpendicular to a direction extending from the first adjustment electrode assembly to the second adjustment electrode assembly.

2. The adjustment aid of claim 1, wherein the excitation electrode and the reception electrode are aligned to overlap one another to form a feed capacitor in an optimally adjusted state of the first component and the second component relative to one another.

3. The adjustment aid of claim 2, wherein the transmission electrode and the evaluation electrode are aligned to overlap one another to form a measuring capacitor in the optimally adjusted state.

4. The adjustment aid of claim 1, wherein the reception electrode and the transmission electrode are connected to one another in an electrically conductive manner.

5. The adjustment aid of claim 1, wherein the first adjustment electrode assembly has a first planar array of electrodes and the second adjustment electrode assembly has a second planar array of electrodes arranged in a plane parallel to the first planar array of electrodes, the first component and the second component are adjusted relative to one another.

6. The adjustment aid of claim 1, wherein the first adjustment electrode assembly has a pair of evaluation electrodes arranged with connecting lines to the excitation electrode that intersect at an angle different from 0°.

7. The adjustment aid of claim 6, further comprising a third evaluation electrode arranged on the connecting line of one of the pair of evaluation electrodes and the excitation electrode.

8. The adjustment aid of claim 7, wherein the excitation electrode and the evaluation electrodes are arranged equidistantly.

9. The adjustment aid of claim 6, wherein the angle of intersection of the connecting lines of the pair of evaluation electrodes to the excitation electrode is greater than 0° and less than 180°.

10. The adjustment aid of claim 1, wherein the second adjustment electrode assembly has a pair of transmission electrodes arranged with connecting lines to the reception electrode that intersect at an angle different from 0°.

11. The adjustment aid of claim 10, further comprising a third transmission electrode arranged on the connecting line of one of the pair of transmission electrodes and the reception electrode.

12. The adjustment aid of claim 11, wherein the reception electrode and the transmission electrodes are arranged equidistantly.

13. The adjustment aid of claim 10, wherein the angle of intersection of the connecting lines of the pair of transmission electrodes to the reception electrode is greater than 0° and less than 180°.

14. The adjustment aid of claim 1, wherein the excitation electrode, the evaluation electrode, the reception electrode, and the transmission electrode have circular and/or elliptical and/or polygonal metallization structures.

15. The adjustment aid of claim 1, wherein the first adjustment electrode assembly is arranged on an outer side of a skin of the human body and the second adjustment electrode assembly is implanted on an inner side of the skin.

16. A wireless connector assembly, comprising:

a first component;

a second component that is implantable; and an adjustment aid aligning the first component and the second component relative to each other, the adjustment aid including a first adjustment electrode assembly having an excitation electrode and a pair of evaluation electrodes, the pair of evaluation electrodes are arranged with connecting lines to the excitation electrode that intersect at an angle greater than 0° and less than 180°, a second adjustment electrode assembly having a reception electrode and a pair of transmission electrodes, the pair of transmission electrodes are arranged with connecting lines to the reception electrode that intersect at an angle greater than 0° and less than 180°, and a control and evaluation circuit connected to the first adjustment electrode assembly, the first adjustment electrode assembly is arranged on the first component, the second adjustment electrode assembly is arranged on the second component, the control and evaluation circuit supplies the excitation electrode with an excitation signal and measures a measurement signal at the evaluation electrode, the measurement signal depends on a degree of overlap between the first adjustment electrode assembly and the second adjustment electrode assembly.

17. The wireless connector assembly of claim 16, wherein the second adjustment electrode assembly has an implantable array of coupling electrodes.

18. The wireless connector assembly of claim 17, wherein the first adjustment electrode assembly has an external array of coupling electrodes that establishes electrical contact with the implantable array of coupling electrodes in an implanted state.

19. The wireless connector assembly of claim 16, wherein the first component is an implantable coaxial plug connector and the second component is an implantable coaxial mating plug connector.

20. The wireless connector assembly of claim 16, wherein the first component is a coaxial socket of a stimulation implant and the second component is a coaxial plug connector of a stimulation electrode.

21. A method for monitoring a position of a first component and a second component relative to one another, comprising:

providing an adjustment aid including a first adjustment electrode assembly having an excitation electrode and a pair of evaluation electrodes, the pair of evaluation electrodes are arranged with connecting lines to the excitation electrode that intersect at an angle greater than 0° and less than 180°, and a second adjustment electrode assembly having a reception electrode and a pair of transmission electrodes, the pair of transmission electrodes are arranged with connecting lines to the reception electrode that intersect at an angle greater than 0° and less than 180°, the first adjustment electrode assembly is arranged on the first component, the second adjustment electrode assembly is arranged on the second component;

applying an excitation signal to the excitation electrode;

measuring a measurement signal at the evaluation electrode; and comparing the measurement signal with a preset threshold value.

22. The method of claim 21, further comprising changing a position of the first component and the second component relative to one another until the measurement voltage exceeds the preset threshold value.

23. The method of claim 22, further comprising generating a warning signal when the measurement signal is below the preset threshold value.

* * * * *